US009668884B2

(12) United States Patent
Simpson et al.

(10) Patent No.: US 9,668,884 B2
(45) Date of Patent: Jun. 6, 2017

(54) METHOD OF MAKING SELF-CLEANING SKIN-LIKE PROSTHETIC POLYMER SURFACES

(71) Applicant: UT-Battelle, LLC, Oak Ridge, TN (US)

(72) Inventors: John T. Simpson, Clinton, TN (US); Ilia N. Ivanov, Knoxville, TN (US); Jason Shibata, Manhattan Beach, CA (US)

(73) Assignee: UT-Battelle, LLC, Oak Ridge, TN (US)

( * ) Notice: Subject to any disclaimer, the term of this patent is extended or adjusted under 35 U.S.C. 154(b) by 430 days.

(21) Appl. No.: 13/975,434

(22) Filed: Aug. 26, 2013

(65) Prior Publication Data

US 2013/0328239 A1  Dec. 12, 2013

Related U.S. Application Data

(62) Division of application No. 13/357,698, filed on Jan. 25, 2012, now abandoned, which is a division of
(Continued)

(51) Int. Cl.
*A61F 2/50* (2006.01)
*A61F 2/76* (2006.01)
(Continued)

(52) U.S. Cl.
CPC .............. *A61F 2/5044* (2013.01); *A61F 2/76* (2013.01); *A61F 2/78* (2013.01); *A61F 2/586* (2013.01);
(Continued)

(58) Field of Classification Search
CPC ........ A61F 2002/5001; A61F 2240/001; A61F 2240/0004; A61F 2/5033; A61F 2/76;
(Continued)

(56) References Cited

U.S. PATENT DOCUMENTS 5,727,567 A  3/1998 Carnaby et al.
7,150,904 B2  12/2006 D'Urso et al.
(Continued)

FOREIGN PATENT DOCUMENTS

KR  WO 2009028745 A1 *  3/2009  .......... B29C 45/372
WO  WO 03013827  2/2003

OTHER PUBLICATIONS

International Search Report of PCT/US2010/040511 Mailed on Oct. 11, 2010 (8 pages).
(Continued)

*Primary Examiner* — Jacob Cigna
*Assistant Examiner* — Lee A Holly
(74) *Attorney, Agent, or Firm* — Brinks Gilson & Lione

(57) ABSTRACT

An external covering and method of making an external covering for hiding the internal endoskeleton of a mechanical (e.g., prosthetic) device that exhibits skin-like qualities is provided. The external covering generally comprises an internal bulk layer in contact with the endoskeleton of the prosthetic device and an external skin layer disposed about the internal bulk layer. The external skin layer is comprised of a polymer composite with carbon nanotubes embedded therein. The outer surface of the skin layer has multiple cone-shaped projections that provide the external skin layer with superhydrophobicity. The carbon nanotubes are preferably vertically aligned between the inner surface and outer surface of the external skin layer in order to provide the skin layer with the ability to transmit heat. Superhydrophobic powders may optionally be used as part of the polymer composite or applied as a coating to the surface of the skin layer to enhance superhydrophobicity.

17 Claims, 9 Drawing Sheets

Related U.S. Application Data application No. 12/495,082, filed on Jun. 30, 2009, now Pat. No. 8,142,516.

(51) Int. Cl.
*A61F 2/78* (2006.01)
*A61F 2/58* (2006.01)

(52) U.S. Cl.
CPC ............. *A61F 2002/5001* (2013.01); *A61F 2002/5055* (2013.01); *A61F 2002/5089* (2013.01); *A61F 2002/7665* (2013.01); *Y10T 428/24612* (2015.01)

(58) Field of Classification Search
CPC .... A61F 2/78; A61F 2/586; A61F 2002/5055; A61F 2002/5089; A61F 2/66; B05D 5/083; B05D 5/08; C03C 15/00; A61L 24/0078; B29C 45/372; B32B 37/00; B08B 17/06
See application file for complete search history.

(56) References Cited

U.S. PATENT DOCUMENTS

| | | | |
|---|---|---|---|
| 7,258,731 B2 | 8/2007 | D'Urso et al. | |
| 2005/0064141 A1* | 3/2005 | Flaig | B32B 37/00 428/141 |
| 2006/0204738 A1 | 9/2006 | Dubrow et al. | |
| 2006/0279191 A1 | 12/2006 | Geohegan et al. | |
| 2007/0031639 A1* | 2/2007 | Hsu | B05D 5/08 428/141 |
| 2008/0145631 A1* | 6/2008 | Bhate | B08B 17/06 428/220 |
| 2008/0154245 A1 | 6/2008 | Martin | |
| 2008/0280137 A1* | 11/2008 | Ajayan | A61L 24/0078 428/375 |
| 2009/0018670 A1 | 1/2009 | Puchhammer | |
| 2009/0042469 A1 | 2/2009 | Simpson | |
| 2009/0043403 A1* | 2/2009 | Asgeirsson | A61F 2/66 623/53 |

OTHER PUBLICATIONS

Article Entitled "Superhydrophobic Carbon Nanotube Forests" by Kenneth K. S. Lau et al., Nano Letters, vol. 3, No. 12, 2003, pp. 1701-1705.

Article Entitled "Artificial Skin Senses Hot and Cold," by Tracy Staedter, from Discovery News dated Mar. 10, 2008, two pages, and identified as XP-002601899.

Kenneth K. S. Lau et al., article entitled "Superhydrophobic Carbon Nanotube Forests," Nano Letters, vol. 3, No. 12, 2003, pp. 1701-1705.

* cited by examiner

METHOD OF MAKING SELF-CLEANING SKIN-LIKE PROSTHETIC POLYMER SURFACES

CROSS REFERENCE TO RELATED APPLICATIONS

The present patent disclosure is a divisional of application Ser. No. 13/357,698 entitled "Method of Making Self-Cleaning Skin-Like Prosthetic Polymer Surfaces", filed Jan. 25, 2012, which is a divisional of application Ser. No. 12/495,082 entitled "Self-Cleaning Skin-Like Prosthetic Polymer Surfaces," filed Jun. 30, 2009, the entire disclosures of which are hereby incorporated by reference.

FEDERALLY SPONSORED RESEARCH AND DEVELOPMENT

The United States Government has rights in this invention pursuant to contract no. DE-AC05-00OR22725 between the United States Department of Energy and UT-Battelle, LLC.

FIELD

This invention relates generally to the field of prosthetics. More specifically, this invention pertains to the use of nanotechnology to create tough, self-cleaning polymer surfaces that simulate skin-like properties for use as a covering for a prosthetic device.

BACKGROUND

Artificial arms and legs, as well as other prostheses attempt to restore normal function to amputees. Part of this normal function is the physical or aesthetic appearance of the prosthetic limb. One major problem with existing prosthetic devices is that their exterior surface does not exhibit many of the characteristics of human skin, such as toughness, flexibility, heat and pressure sensation, water repellency, and smoothness. The lack of toughness and flexibility in existing prostheses causes the exterior surface of these prostheses to wrinkle or become distorted when they are stretched or compressed. In addition, the polymers currently used in making the prosthetic covering, generally behave as a thermal insulator, thereby preventing the quick detection and transmittal of thermal readings to embedded heat sensors. This time lapse often creates a problem by allowing the polymer to begin melting before the embedded thermal sensor can detect a change in temperature.

Accordingly, while significant advances have been made in the prosthetic industry over the past decade, there exists a continual desire to provide prostheses with enhanced performance and aesthetic appeal. In particular, a prosthetic device having an exterior surface that exhibits the characteristics of real human skin is highly desirable.

SUMMARY

The present disclosure provides an external covering for hiding the internal endoskeleton of a mechanical device (e.g., prosthetic device) that provides skin-like qualities. One embodiment of an external covering constructed in accordance with the teachings of the present disclosure, generally comprises an internal bulk layer in contact with the endoskeleton of the mechanical device and an external skin layer disposed about the internal bulk layer. The external skin layer is comprised of a polymer composite with carbon nanotubes embedded therein. The outer surface of the skin layer has multiple cone-shaped projections that provide the external skin layer with superhydrophobicity. The carbon nanotubes are preferably vertically aligned between the inner surface and outer surface of the external skin layer in order to provide the skin layer with enhanced thermal conductivity, i.e., the ability to transmit heat. The mechanical properties exhibited by the external skin layer may be enhanced by selecting the orientation or alignment angle for the carbon nanotubes in the skin layer. The mechanical properties may further be enhanced by exposing the carbon nanotubes to a high temperature annealing procedure. According to another aspect of the present disclosure, a superhydrophobic powder may optionally be used as part of the skin layer or applied as a coating to the surface of the skin layer to enhance superhydrophobicity of the skin layer.

Another embodiment of the present disclosure provides a method of making the external covering described above for use with a mechanical device whose surface exhibits skin-like qualities. This method generally comprises providing a mold having a cavity with a predetermined shape and at least one surface having a nano-funnel or micro-funnel patterned array. A film comprised of a polymer composite with embedded carbon nanotubes is inserted into the cavity of the mold and allowed to contact the patterned surface of the mold's cavity. Then heat, vacuum, pressure, or a combination thereof is applied to the cavity and/or the film to cause the film to conform to the predetermined shape of the mold and to induce the formation of superhydrophobic cone-shaped projections on the surface of the film. After the shaped film is cooled and removed from the mold, it is adhered to a pre-shaped internal bulk layer to form the external covering.

According to another aspect of the present disclosure the step in which the shaped film is adhered to the pre-shaped internal bulk layer may be replaced with the step of back-molding the internal back layer to be in contact with the film. According to yet another aspect of the present disclosure, the method may further comprise the step of opening a gap in the mold and injecting an in-mold coating into the gap to coat the surface of the film.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figures 1A, 1B:
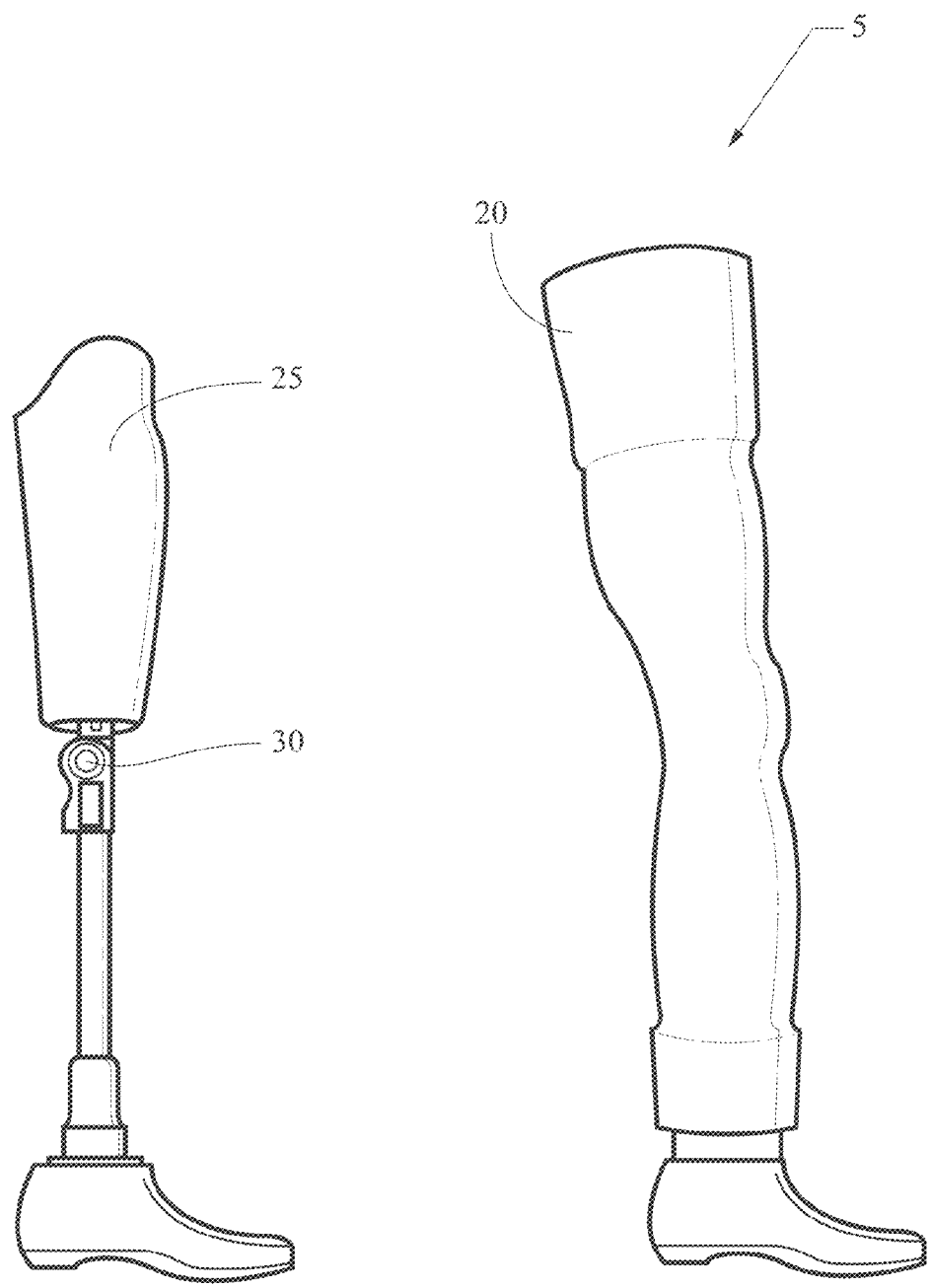
FIG. 1A is a perspective view of an endoskeleton for a transtibial prosthetic device.
FIG. 1B is a perspective view of a prosthetic device made according to the teachings of the present disclosure that includes the endoskeleton of FIG. 1A.
Figure 2A:
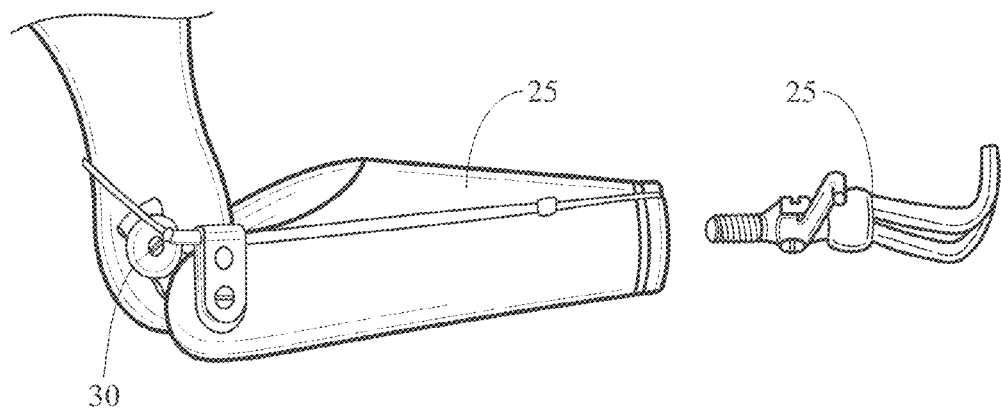
FIG. 2A is a perspective view of an endoskeleton for a transhumeral prosthetic device.
Figure 2B:
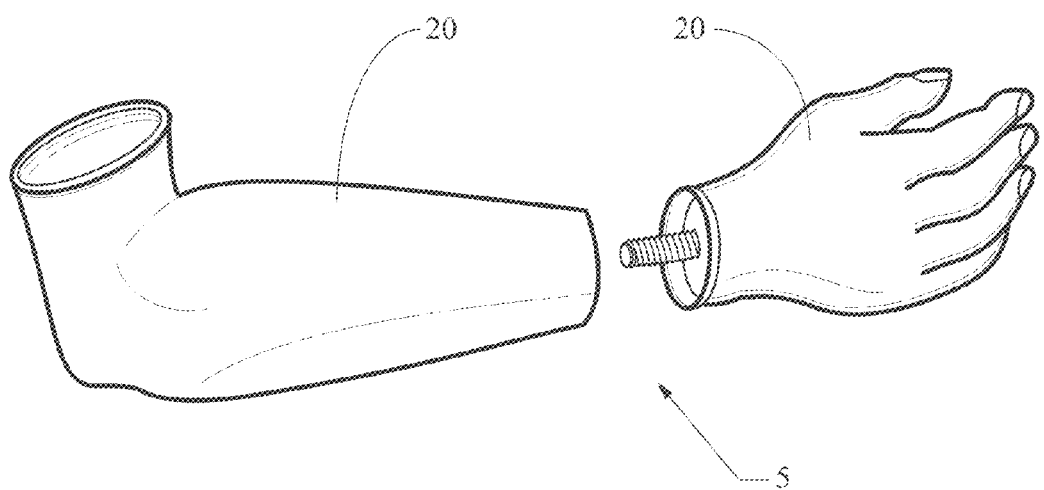
FIG. 2B is a perspective view of a prosthetic device made according to the teachings of the present disclosure that includes the endoskeleton of FIG. 2A.

The following description is merely exemplary in nature and is in no way intended to limit the present disclosure or its application or uses. It should be understood that throughout the description and drawings, corresponding reference numerals indicate like or corresponding parts and features.

The present disclosure generally provides an external covering for a mechanical device, such as a prosthetic device, used as a replacement for a human limb that requires the outer layer of the prosthesis to have a skin-like exterior surface. As shown in FIGS. 1(A-B) and 2(A-B), examples of such prostheses 5 include, but are not limited to, those used as transtibial, transfemoral, transradial, or transhumeral replacements for human limbs. By definition, transtibial and transfemoral prostheses replace legs that are missing from below the knee and from above the knee, respectively. Likewise, transradial and transhumeral prostheses replace arms missing from below the elbow and from above the elbow, respectively. In FIGS. 1(A-B) and 2(A-B) the prostheses shown are transfemoral and transhumeral prostheses, respectively. One skilled-in-the-art will understand that the external covering 20 for a prosthesis as described in this disclosure may be incorporated with any type of prosthesis 5 used as a replacement for a human limb that requires a skin-like exterior surface. One skilled-in-the-art will further understand that the external covering of the present disclosure may be used with the endoskeleton or internal support structure associated with other types of mechanical devices or equipment without departing from scope of the invention.

The prosthetic device 5 is comprised of an internal endoskeleton 25 or pylon structure that may include joints 30, as well as a means (e.g., belts, cuffs, etc.) to attach the prosthesis to the human body. The internal endoskeleton 25 is then covered with an external covering 20 to provide physical protection for the endoskeleton 25 and to aesthetically provide a skin-like appearance. The prosthesis may be integrated with the functioning of the human body through the use of various biosensors, signal controllers, and actuators. The endoskeleton 25 may be made from any light weight material, such as plastics, metals, or alloys. Examples of such light weight materials include polypropylene, titanium, aluminum, and carbon fiber composites.

Figure 3A:
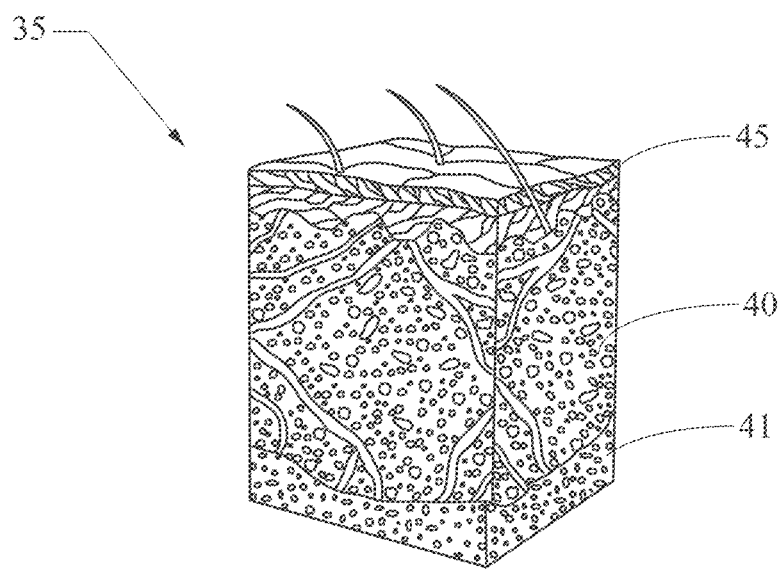
FIG. 3A is a cross-sectional view of human skin highlighting the dermis and epidermis layers.

The external covering 20 is designed and adapted to resemble the appearance and performance of human skin. As shown in FIG. 3A, real human skin 35 is generally comprised of an inner bulk layer called the dermis layer 40 and an outer thin layer called the epidermis layer 45. The dermis layer 40 is in contact with subcutaneous tissue 41 of the human body. The epidermis layer 45 contains a melanin pigment that helps to counteract the absorption of the light rays from the sun by darkening the color of the skin 35.

Figure 3B:
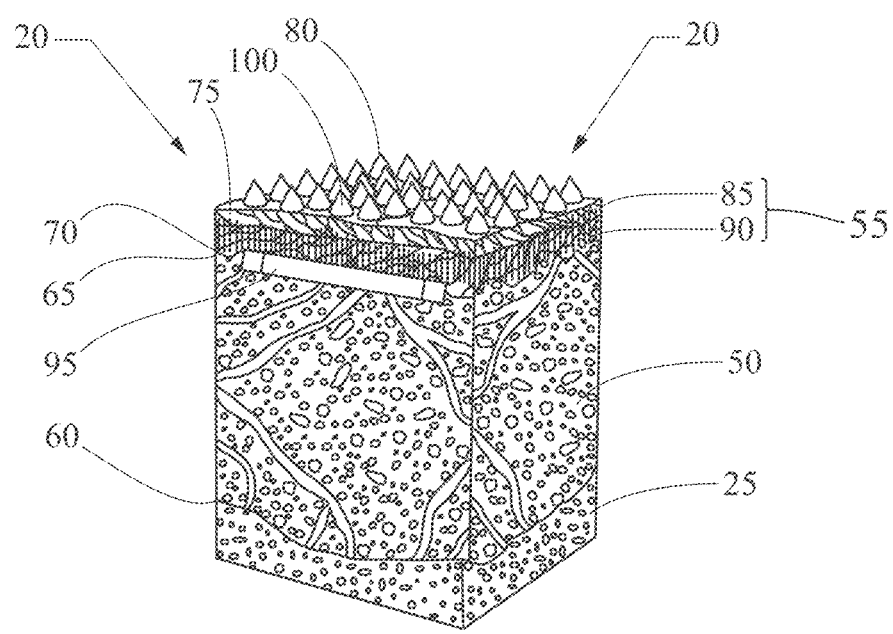
FIG. 3B is a cross-sectional view of an external covering made according to the teachings of the present disclosure.

Similar to human skin 35, the external covering 20 of the current disclosure is comprised of multiple layers as shown in FIG. 3B. Primarily, the external covering 20 comprises an internal bulk layer 50 and an external skin layer 55. The internal bulk layer 50 has a first side 60 and second side 65 with the first side 60 being in contact with the internal endoskeleton 25 of the prosthetic device 5. The external skin layer 55 is disposed about the second side 65 of the internal bulk layer 50. The external skin layer 55 has an inner surface 70 and an outer surface 75. The inner surface 70 being in contact with the second side 65 of the bulk layer 50 and the outer surface 75 representing the external surface of the prosthetic device 5.

Figure 4A:
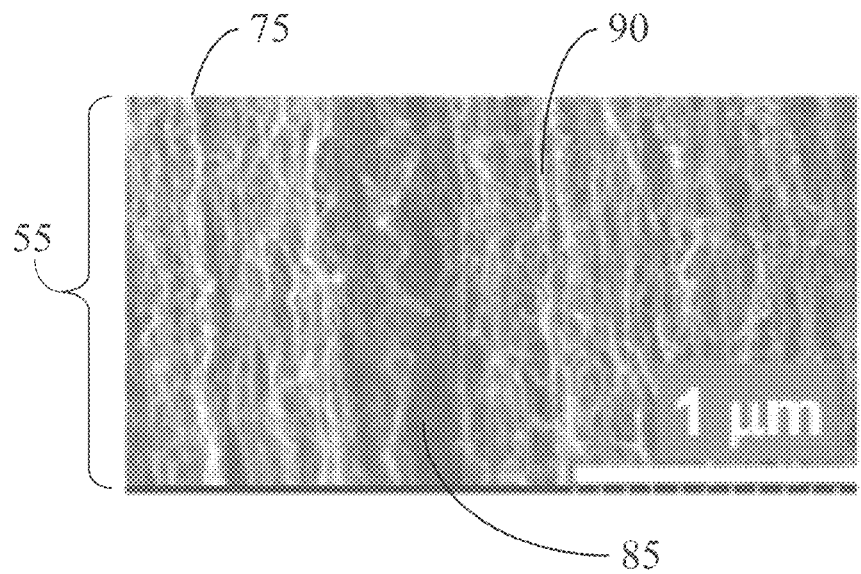
FIG. 4A is a cross-sectional micrograph image of the external skin layer associated with the external covering of FIG. 3B.

The outer surface 75 of the external skin layer 55 exhibits a nano-cone or micro-cone pattern 80 or structure. The external skin layer 55 is further comprised of a polymer composite 85 and an embedded network of carbon nanotubes 90. The carbon nanotubes 90 are preferably vertically aligned or in other words, positioned to be about perpendicular to the outer surface 75 as shown in FIG. 4A. The carbon nanotubes 90 may occupy from about 1% to about 40% of the volume associated with the external skin layer 55.

The nano-cone or micro-cone 80 pattern represents nanometer or micrometer size surface irregularities predetermined to be located on the outer surface 75 of the prosthetic device 5. These nano-cone or micro-cone 80 irregularities may be protrusions arising out of the outer surface 75 of the external skin layer 55. These irregularities, which are formed as an integral part of the external skin layer 55, may vary the height, spacing, shape, and characteristics of this layer's outer surface 75.

Embedding carbon nanotubes 90 into the external skin layer 55 of the prosthesis 5 provides for enhanced features, such as toughness, strength, and durability. In fact, the external skin layer 55 is designed to be tougher and stronger than the internal bulk layer 50. The carbon nanotubes 90 exhibit high tensile strength and elastic modulus in the axial direction, while being relatively soft in the radial direction. Thus the external skin layer 55 may exhibit a tough outer surface 75, while maintaining a relatively high degree of flexibility.

Figures 4B, 4C:
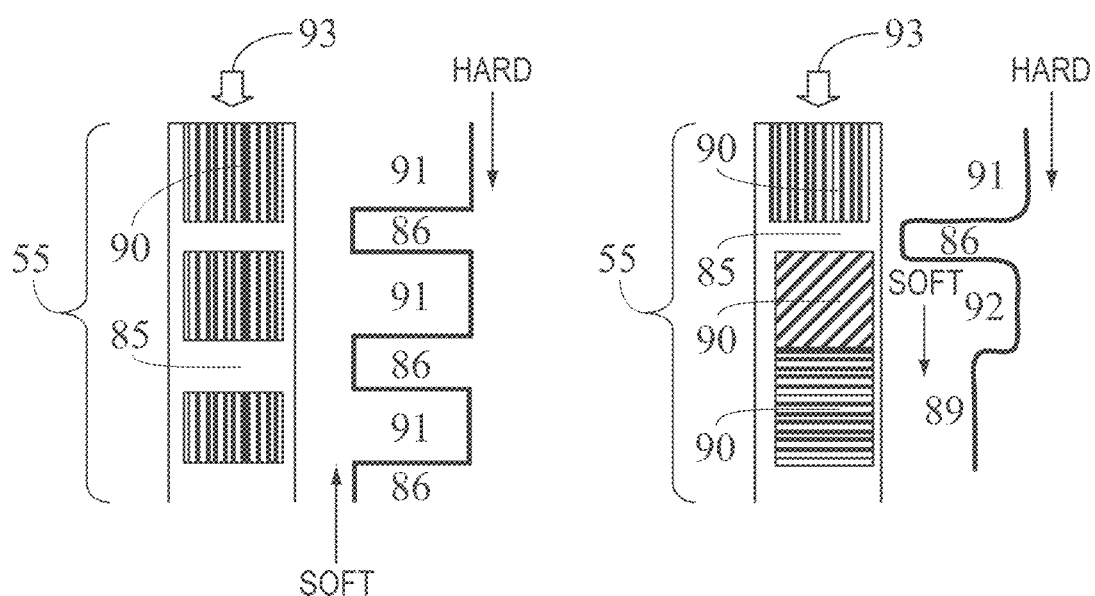
FIG. 4B is a cross-sectional schematic representation of an external skin layer prepared according to one aspect of the present disclosure highlighting both hard and soft segments.
FIG. 4C is a cross-sectional schematic representation of an external skin layer highlighting possible differences in orientation for the carbon nanotubes in the polymer composite according to one aspect of the present invention.

The external skin layer 55 may be constructed to exhibit a gradient in mechanical properties by controlling the orientation or alignment of the carbon nanotubes 90, as well as the spacing between the nanotubes 90 embedded in the polymer composite 85 of the skin layer 55. Referring to FIG. 4B, the external skin layer 55 may comprise multiple layers of embedded nanotubes 90 and layers of polymer composite 85 that are absent of any nanotubes 90. When the nanotubes 90 are vertically aligned with the outer surface 75 of the external skin layer 55 they represent a tough, hard segment or layer 91. In comparison, the polymer composite 85 absent any nanotubes 90 represents a relatively soft segment or layer 86. In other words, the mechanical properties exhibited by a layer of the polymer composite 85 with embedded nanotubes 90 is enhanced over the pure polymer properties of the composite 85 layer. Embedding carbon nanotubes 90 into the polymer composite 85 provides for anisotropic enhancement of the mechanical properties exhibited by the external skin layer 55. The extent of this enhancement depends upon the directional alignment of the nanotubes 90, the structure or type of nanotubes 90, the amount or loading of nanotubes 90 in the external skin layer 55, and the composition of the polymer composite 85, among other factors. In fact, the extent of this enhancement may be larger when a relatively "soft" polymer composite 85 is used and smaller when a relatively "hard" polymer composite 85 is used.

When the carbon nanotubes 90 are vertically aligned with the outer surface 75 of the external skin layer 55, they are orientated in a direction that is parallel to the applied load 93, thereby, providing for a large enhancement in mechanical properties. As shown in FIG. 4C, a layer 89 in which the embedded carbon nanotubes 90 are perpendicular (90°) to the mechanical load 93 will not be as "hard" as a layer 91 where the nanotubes 90 are parallel (0°) to the mechanical load 93 and not as "soft" as a layer 86 comprised of the pure polymer composite 85. Carbon nanotubes 90 that are perpendicular to the mechanical load 93 are aligned to be parallel with the outer surface 75 of the external skin layer 55. An intermediate enhancement in mechanical properties may result when the layer 92 has nanotubes 90 oriented in a direction that is between the vertical (0°) alignment of layer 91 and the perpendicular (90°) alignment of layer 89. In FIG. 4C, the intermediate layer 92 is shown with nanotubes 90 aligned at a 45° angle to the mechanical load 93. One skilled-in-the-art will understand that the carbon nanotubes 90 may be aligned or oriented with respect to the mechanical load 93 at any angle between 0° and 90°.

For example, the mechanical properties exhibited by an external skin layer 55 comprising about 10 wt. % multiwalled carbon nanotubes 90 in an epoxy polymer composite 85 were measured at about 25° C. using a nanoindentor equipped with a Berkovich tip. A summary of the enhancement in mechanical properties observed for the external skin layer 55 upon incorporation of carbon nanotubes 90 into the polymer composite 85 is plotted in FIG. 5A as a function of nanotube 90 alignment with respect to the direction of the applied load 93. The origin point 105 of the plot (e.g., 0% enhancement) represents the mechanical properties exhibited by the pure polymer composite 85 without the incorporation of any carbon nanotubes 90. Upon the incorporation of nanotubes 90 into the polymer composite 85 an enhancement in mechanical properties, such as Young's modulus 110, hardness 111, polymer creep 112, and scratch resistance 120, is observed. An enhancement in polymer creep may be defined as a reduction in the permanent deformation of the polymer that occurs when the polymer composite 85 is exposed to a constant applied stress.

Figure 5A:
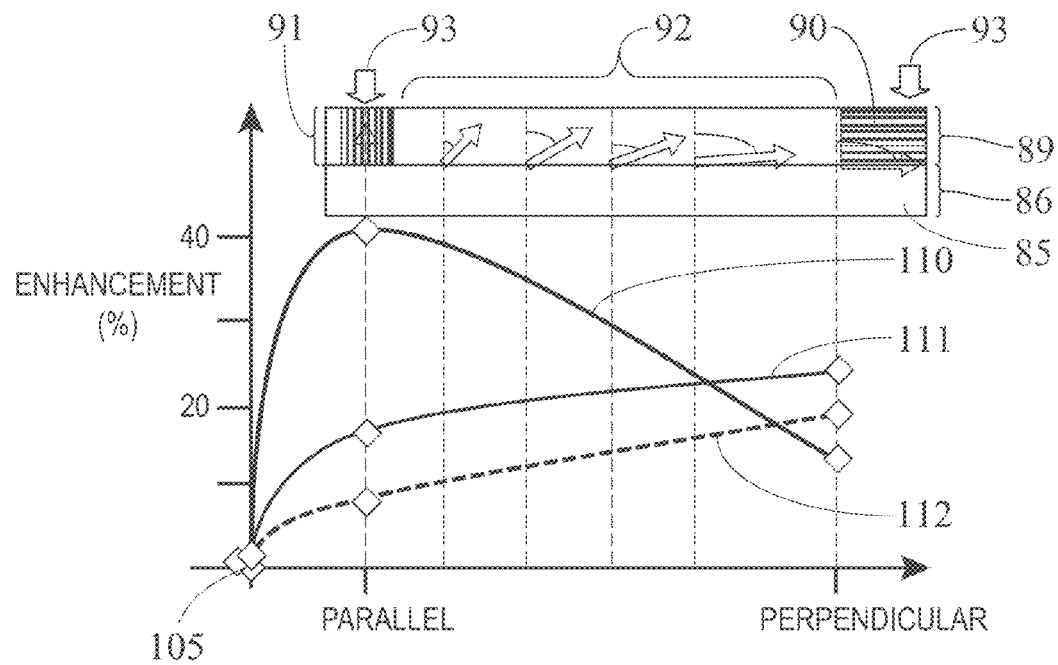
FIG. 5A is a graphical representation of the enhancement obtained in the mechanical properties of the external skin layer plotted as a function of carbon nanotube orientation.

Referring to FIG. 5A, the maximum enhancement in Young's modulus 110 of 40% occurs when the carbon nanotubes 90 are aligned parallel with the applied load 93. The hardness of the external skin layer 55 can be increased between about 17% to about 25% compared to the pure polymer composite 85 upon the incorporation of nanotubes 90 into the polymer composite 85 with the largest enhancement occurring when the nanotubes 90 are aligned perpendicular to the load 93. Similarly, the largest enhancement with respect to reducing polymer deformation or creep 112 is provided when the embedded carbon nanotubes 90 are aligned perpendicular to the applied load 93.

An optional high temperature annealing procedure that exposes the carbon nanotubes 90 to a temperature up to about 2,400° C. can be used to further enhance the mechanical properties exhibited by the external skin layer 55. It is possible that exposure of the nanotubes 90 to this annealing procedure reduces the existence of surface/wall defects in the nanotubes 90, which in turn increases the crystallinity and overall stiffness of the nanotubes 90. Thus this annealing procedure can be used to enhance the mechanical properties exhibited by the external skin layer 55 with having to alter the orientation of the nanotubes 90 in the layer 55.

Figure 5B:
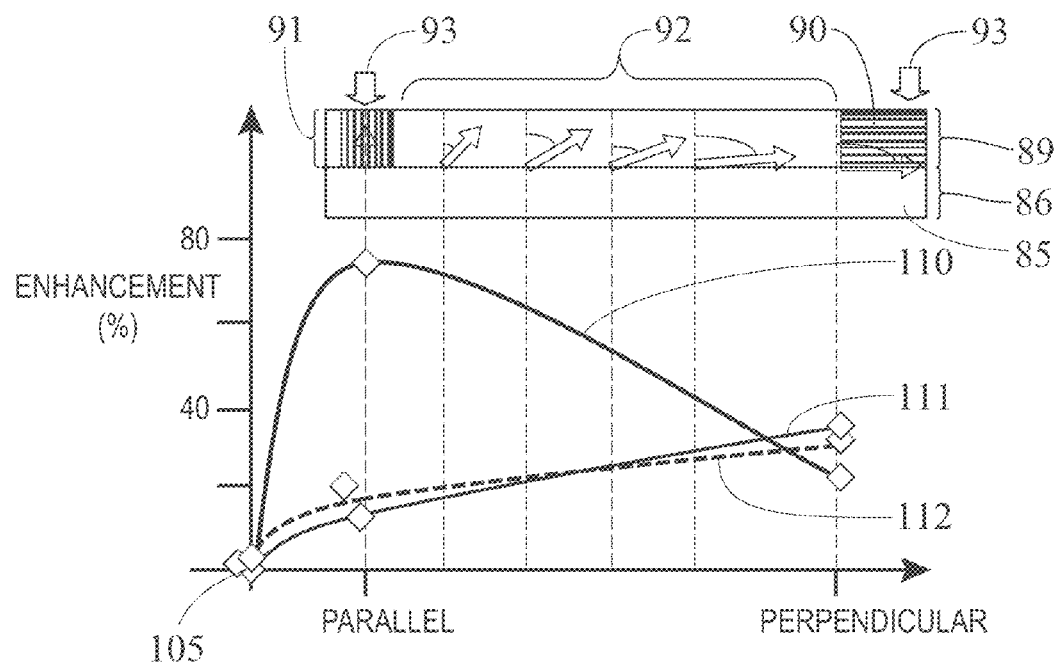
FIG. 5B is a graphical representation of the enhancement obtained in the mechanical properties of the external skin layer plotted as a function of carbon nanotube orientation after the nanotubes are exposed to a high temperature, annealing procedure.

Referring now to FIG. 5B, after annealing the carbon nanotubes an enhancement of about 71% in Young's modulus 110 is observed when about 10 wt. % of the carbon nanotubes 90 are embedded in the polymer composite 85 and are aligned parallel to the applied load 93. The hardness of the external skin layer 55 with embedded carbon nanotubes can be increased up to about 34% over the pure polymer composite 85, and polymer deformation or creep 112 can be reduced by about 29% when the carbon nanotubes 90 are annealed and then aligned perpendicular to the applied load 93.

The overall range of enhancement for Young's modulus 110, hardness 111, and polymer creep 112 attributable to annealing the carbon nanotubes 90, aligning the nanotubes 90 in the polymer composite 85, or a combination of both is between about 22 to 80%, about 13 to 34%, and about 13 to 29%, respectively, when about 10 wt. % nanotubes 90 are incorporated into the polymer composite 85 of the external skin layer 55. Further enhancement of the mechanical properties can occur upon the incorporation of a greater weight percentage of carbon nanotubes 90 into the polymer composite 85. The incorporation of about 40 wt. % carbon nanotubes 90 into the polymer composite 85 may increase Young's modulus 110, increase hardness 111, and reduce polymer creep 112 by as much as about 320%, 134%, and 116%, respectively.

Figure 5C:
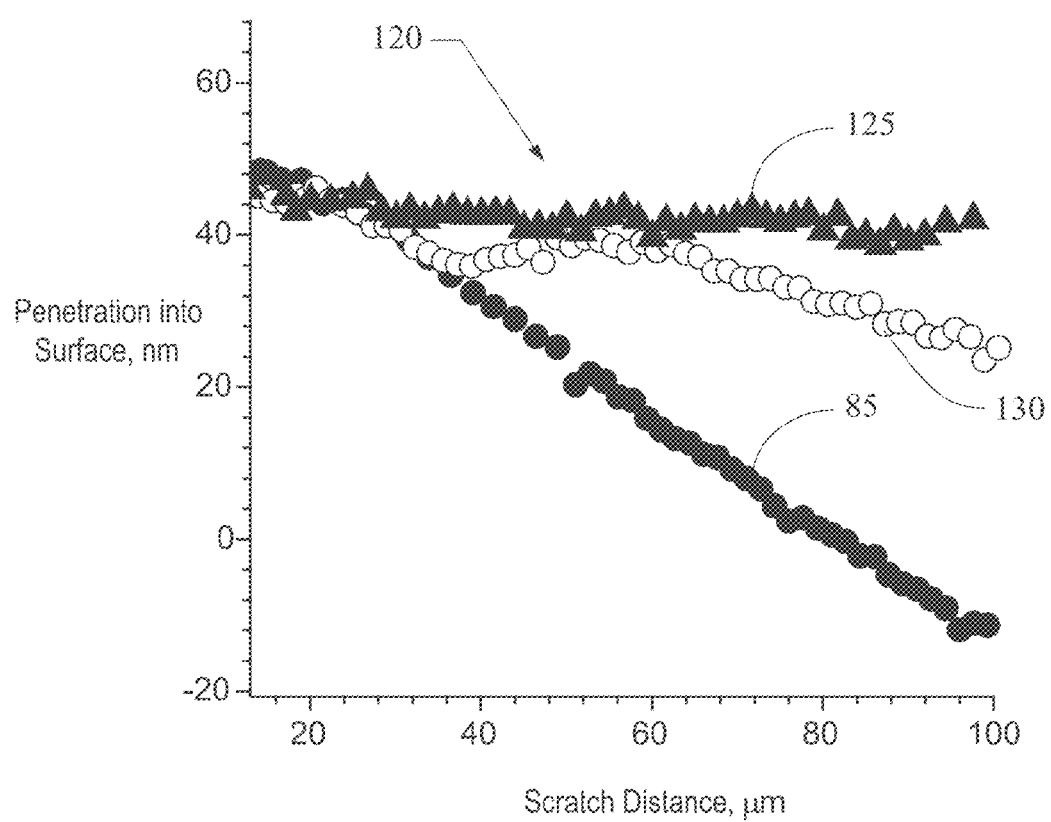
FIG. 5C is a graphical representation of the scratch resistance obtained for the external skin layer at various carbon nanotube orientations depicted as the amount of penetration plotted as a function of scratch distance.

Referring now to FIG. 5C, the effect of the alignment or orientation of carbon nanotubes in the external skin layer 55 on improving the scratch resistance 120 exhibited by the skin layer is shown. Carbon nanotubes 90 oriented perpendicular 125 to the scratch direction in an epoxy polymer composite 85 provide about a 90% reduction in surface penetration when compared to the pure polymer composite 85. When the carbon nanotubes 90 are oriented parallel 130 to the scratch direction, the reduction of surface penetration is about 58%. One skilled-in-the-art will understand that although the scratch conditions utilized were 0.1 mN load over 100 mm distance at 0.5 mm/s, similar results would be obtained using a different set of standard conditions. The scratch resistance can be further tuned by controlling the type of nanotube (e.g., single nanotube, few wall nanotubes, or double wall nanotubes), as well as controlling the weight loading, the incorporation of other additives (i.e., metal oxide structures) on the surface or between nanotubes.

The external skin layer 55 with embedded carbon nanotubes 90 can also conduct heat and provide for pressure sensation. The presence of the carbon nanotubes 90 enhances the ability of the outer surface 75 to conduct electrical current and heat. Thus a variety of different sensors 95 may be optionally located in the internal bulk layer 50 that can detect temperature or pressure changes occurring in the external skin layer 55, thereby, imitating the performance of real skin nerve cells.

The nano-cone or micro-cone 80 patterns provide the outer surface 75 of the external skin layer 55 with superhydrophobicity, thereby, keeping the external surface of the prosthesis clean and dry. The superhydrophobicity of the outer surface 75 is preferably described as the surface having a contact angle greater than about 150 degrees when a drop of water is applied to the surface.

Referring to FIG. 3B, superhydrophobic powders 100 may optionally be incorporated into or onto the outer surface 75 of the external skin layer 55, thereby providing an additional mechanism through which water may be repelled. Preferably, the superhydrophobic powders 100 comprise at least one hydrophobic material selected as one from the group of perfluorinated organics, fluorinated organics, and self-assembled monolayers. Other examples of superhydrophobic powders include those described in U.S. Publication No. 2009/0042469, herein incorporated by reference.

Carbon nanotubes 90 exhibit a range of different colors depending on their size, shape, and length. The carbon nanotubes 90 may be sorted and selected by size to provide a predetermined color to the external skin layer 55. Thus the external skin layer 55 may be designed to match the color associated with the rest of a person's skin 35, thereby, making the external surface of the prosthesis appear much more skin-like and natural.

The carbon nanotubes 90 as embedded in or applied to the external skin layer 55 may be single-wall (SWNTs) or multiwall (MWNTs) structures exhibiting either metallic conducting or semiconducting behavior. Carbon nanotubes are allotropes of carbon having a nanostructure with a large length to diameter ratio. Preferably, the diameter of the nanotubes is on the order of a few nanometers with a length up to several millimeters. Preferably, the carbon nanotubes are vertically aligned or, in other words, perpendicular to the outer surface 75 of the external skin layer 55 in order to enhance the desired affects. The nanotubes are embedded in a polymer composite 85 or in an applied surface coating in a manner that stabilizes the architecture of the nanotubes 90 in the predetermined vertical alignment, direction, or pattern.

The carbon nanotubes 90 can be grown from or deposited by plasma enhanced chemical vapor deposition (PECVD) or any other method known to one skilled-in-the-art, including but not limited to chemical vapor deposition, arc discharge, laser ablation, high pressure carbon monoxide (HiPCO), spray coating, dip coating, and flow coating.

The polymer composite 85 of the exterior skin layer 55 or optionally a coating applied to the outer surface 75 of the exterior skin layer 55 may be made of any known thermoplastic or elastomeric material, such as polyimides, fluoropolymers, polyamides, polyesters, silicones, polyurethanes, epoxies, or polyacrylates, among others. Preferably, the polymer composite or coating is comprised of a polyimide material.

The interior bulk layer 50 may be comprised of any fabric, foam, silicone, gelatin, latex, collagen, sponge, wool, cotton, or a mixture or combination thereof. One skilled-in-the-art will understand that the interior bulk layer 50 may be comprised of any other material that will provide for the physical protection of the underlying endoskeleton 25 without departing from the scope of this disclosure.

The exterior skin layer 55 may be fastened to the underlying interior bulk layer 50 and the interior bulk layer 50 may be fastened to the underlying endoskeleton 25 by any means known to one skilled-in-the-art. Such means includes, but is not limited to, the use of adhesives, coupling agents, mechanical fasteners, and melt bonding.

Figure 6A:
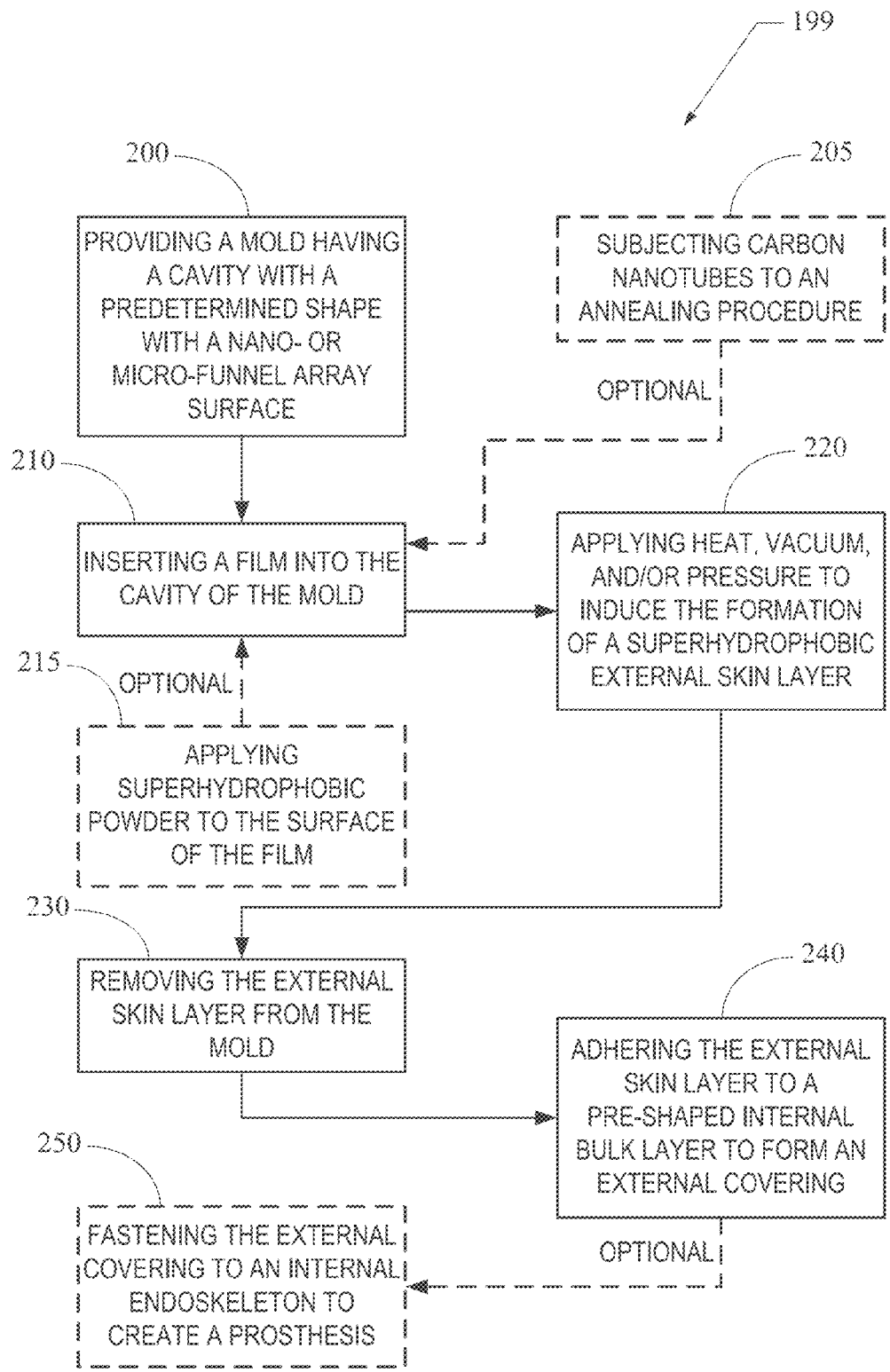
FIG. 6A is a flowchart of a manufacturing process for an exterior covering for use in a mechanical (e.g., prosthetic) device according to one embodiment of the present disclosure.

It is another objective of the present disclosure to provide a method 199 of making or manufacturing an exterior covering 20 for use with an endoskeleton 25 to form a mechanical device, such as a prosthetic device 5. One aspect of the present disclosure is to provide a method of forming a prosthesis 5 that includes the previously described exterior covering 20. Referring to FIG. 6A, a method of forming an external covering 20 for use with a mechanical (e.g., prosthetic) device generally comprises the steps of providing 200 a mold having a cavity with a predetermined shape. The mold includes at least one surface having a nano-funnel or micro-funnel array. A more detailed description of the nano-funnel or micro-funnel array surface of the mold as used herein is provided in U.S. patent application Ser. No. 11/945,865 filed Nov. 27, 2007, which is hereby incorporated by reference.

A film, which will form the external skin layer 55, is then inserted 210 into the cavity of the mold. In such, this film is comprised of the polymer composite 85 embedded with carbon nanotubes 90. If desirable, the carbon nanotubes may be optionally subjected to an annealing 205 procedure prior to being incorporated into the film. Optionally, superhydrophobic powder 100 may be applied 215 to the surface of the film. Heat, vacuum, and/or pressure are then applied 220 to induce the formation of an external skin layer 55 exhibiting a superhydrophobic outer surface 75. The application of heat may be accomplished by heating the mold or heating the film. The surface of the film is caused to melt or deform and to take on the shape of the funnel array surface of the mold. The translation of the mold nano-funnel or micro-funnel surface onto the film results in the formation of nano-cones or micro-cones 80 on the outer surface 75 of the external skin layer 55. The external skin layer 55 is then removed 230 from the mold. One skilled-in-the-art will understand that the preceding steps 200, 210, 215, and 220 associated with forming the external skin layer 55 may be varied according to any known steps used in a thermoforming process without departing from the scope of this disclosure.

The external skin layer 55 is then fastened or adhered 240 to a pre-shaped internal bulk layer 50 to form the external covering 20 for use in a prosthetic device 5. Optionally, the formation of a prosthetic device 5 may be completed by fastening 250 the internal bulk layer 50 of the external covering 20 to an endoskeleton 25. One skilled-in-the art will understand that the external covering 20 may be applied to an endoskeleton 25 that represents the internal structure or support for other types of mechanical devices and is not limited to use only with prosthetic devices 5.

Figure 6B:
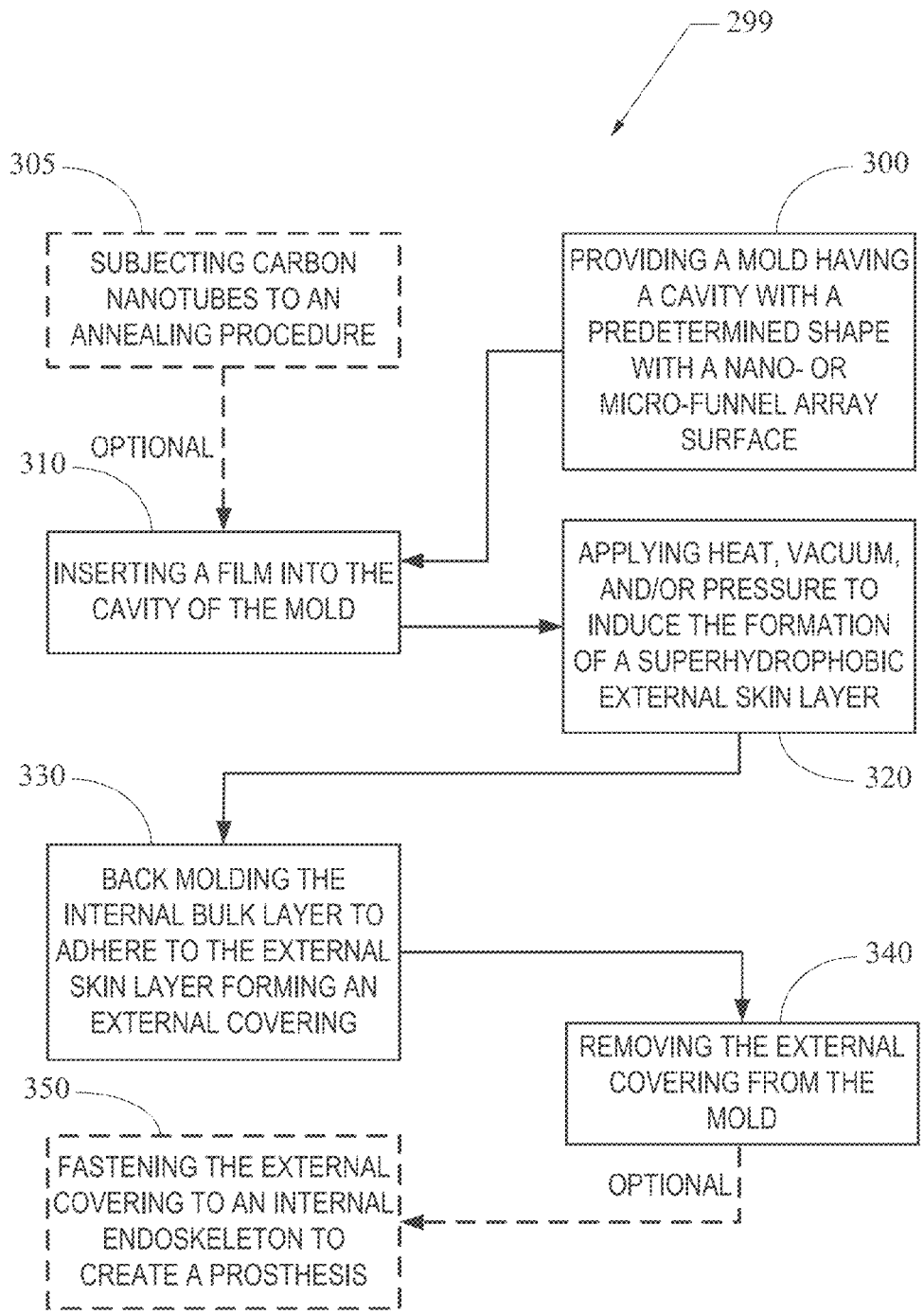
FIG. 6B is a flowchart of a manufacturing process for an exterior covering for use in a mechanical (e.g., prosthetic) device according to another aspect of the present disclosure.

According to another aspect of the present disclosure, a method 299 resembling a film-insert molding or in-mold decorating process may be utilized. Referring now to FIG. 6B, in this method 299 a mold is provided 300 having a cavity with a predetermined shape. This mold includes at least one surface having a nano-funnel or micro-funnel array as previously described.

A film, which will form the external skin layer 55, is then inserted 310 into the cavity of the mold. In such, this film is comprised of the polymer composite 85 embedded with carbon nanotubes 90. If desirable, the carbon nanotubes may be optionally subjected to an annealing 305 procedure prior to being incorporated into the film. Optionally, superhydrophobic powder 100 may be included on the surface of this film. Heat, vacuum, and/or pressure may then be applied 320 to induce the formation of an external skin layer 55 exhibiting a superhydrophobic outer surface 75. The heat may be applied by heating the mold or heating the film. The surface of the film is caused to melt or deform and to take on the shape of the funnel array surface of the mold. The translation of the mold nano-funnel or micro-funnel surface onto the film results in the formation of nano-cones or micro-cones 80 on the outer surface 75 of the external skin layer 55.

Finally, the internal bulk layer 50 may be back-molded 330 onto the external skin layer 55 to form the external covering 20. The internal bulk layer 50 may adhere to the external skin layer 55 by melt bonding or by adhesion when the film includes an adhesive on the surface that is forced into contact with the internal bulk layer 50 during the back-molding step. The external covering 20 is then removed 340 from the mold to complete the process 299 of forming an external covering 20 for a prosthetic device 5. Optionally, the formation of the prosthetic device 5 may then be completed by fastening 350 the internal bulk layer 50 of the external covering 20 to the endoskeleton 25. One skilled-in-the-art will understand that the preceding steps 300, 310, 320, and 330 associated with forming the external skin layer 55 may be varied according to any known steps used in a film-insert molding process without departing from the scope of this disclosure.

According to yet another aspect of the present disclosure, a method 399 that integrates the film-insert molding method 299 with an in-mold coating delivery system may be utilized. In order to effectively apply a coating during the molding operation, a rotating stack mold with at least one needle gate to inject the coating formulation is preferably used along with a coating metering unit or delivery cart.

Figure 6C:
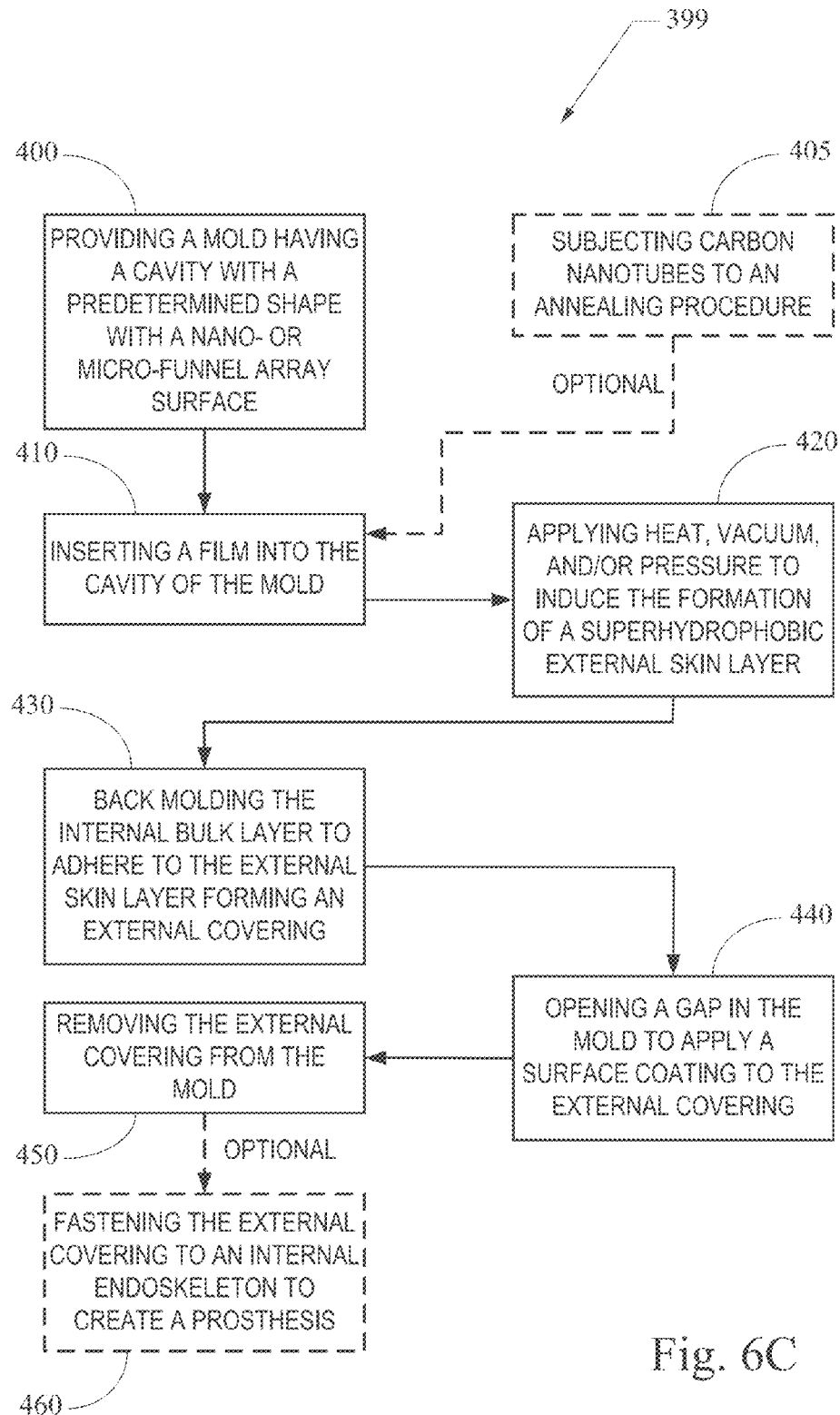
FIG. 6C is a flowchart of a manufacturing process for an exterior covering for use in a mechanical (e.g., prosthetic) device according to yet another aspect of the present disclosure.

Referring now to FIG. 6C, in this method 399 a mold is provided 400 that has a cavity with a predetermined shape and at least one surface having a nano-funnel or micro-funnel array as previously described. The film, which will form the external skin layer 55, is then inserted 410 into the cavity of the mold. If desirable, the carbon nanotubes may be optionally subjected to an annealing 405 procedure prior to being incorporated into the film. Heat, vacuum, and/or pressure may then be applied 420 to induce the formation of an external skin layer 55 exhibiting a superhydrophobic outer surface 75. The internal bulk layer 50 is then back molded 430 onto the external skin layer 55 to form the external covering 20. The internal bulk layer 50 may adhere to the external skin layer 55 by melt bonding or by any other known means.

Finally, a very small mold gap (depending on the desired coating thickness) is then opened 440 and a measured amount of an in-mold coating (IMC) is injected into the gap. The IMC coating can be injected between the outer surface 75 of the external skin layer 55 and the surface of molding containing the nano-funnel or micro-funnel surface. The mold is then closed, clamped, coin/compressed, and the coating cured. Depending on the specific formulation of the IMC coating and the required cure conditions, additional heating or cooling of the mold may be necessary to fully cure the coating. In this way the coating will upon cure exhibit the contour of a nano-cone or micro-cone surface rather than cause the planarization of the outer surface 75. Optionally, this coating may include superhydrophobic powder 100 as a filler material. One skilled-in-the-art will understand that the preceding step of applying 440 an in-mold coating to the outer surface 75 of the external skin layer 55 may be varied according to any known steps used in an in-mold coating process without departing from the scope of this disclosure. In addition, multiple additional steps related to coining and clamping may be required. It is further understood that the in-mold coating step described above may also be incorporated into the thermoforming method described in FIG. 4A.

Finally, the external covering 55 is cooled, the mold opened, and the covering 55 removed 450 from the mold. Optionally, the formation of the prosthetic device 5 may then be completed by fastening 460 the internal bulk layer 50 of the external covering 20 to an endoskeleton 25.

One skilled-in-the-art will understand that the foregoing description is not intended to limit the use of the external covering to the application of prosthetic devices. Rather the external covering of the present disclosure is equally applicable for use in other applications, such as a covering for an endoskeleton, which may include, but not be limited to, mechanical equipment, mechanical devices, or other mechanical structures, that are used in or by other industries, such as automotive or aerospace. For example, the external covering may be applicable for use as a seat covering or an overlay for a dashboard or instrument panel to name a few.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of making an external covering for use with a mechanical device that provides the external surface of the device with an external skin layer, the method comprising the steps of:

providing a mold having a cavity with a predetermined shape and at least one surface having a pattern selected as one from the group of a nano-funnel array, micro-funnel array, or combination thereof;

inserting a film into the cavity of the mold, the film being comprised of a polymer composite with carbon nanotubes embedded therein and oriented such that the external skin layer exhibits a gradient in mechanical properties; wherein the film has a first side and a second side; the first side of the film being in contact with the patterned surface of the mold's cavity;

applying one selected from the group of heat, vacuum, pressure, or a combination thereof to the cavity or the film to form the film into the predetermined shape and to induce the formation of cone-shaped projections on the first side of the film;

back-molding an internal bulk layer to be in contact with the second side of the film, thereby, forming the external covering; the internal bulk layer comprising a flexible material that can conform to the shape of the mechanical device and be fastened thereto;

cooling and removing the external covering from the mold;

wherein the cone-shaped projections provide the external skin layer with superhydrophobicity, while the embedded carbon nanotubes provide the external skin layer with the ability to transmit heat and enhanced mechanical properties as compared to an external covering comprising a polymer composite film of similar composition but absent the embedded carbon nanotubes; the enhanced mechanical properties being defined as an anisotropic increase in Young's modulus, hardness, and scratch resistance, and an anisotropic decrease in polymer creep.

2. The method of claim 1, further comprising the step of annealing the carbon nanotubes prior to the nanotubes being embedded into the polymer composite film, such that the external skin layer with the annealed carbon nanotubes exhibits an anisotropic decrease in polymer creep and an anisotropic increase in Young's modulus and hardness that are larger in magnitude than the values exhibited by the external skin layer when the carbon nanotubes have not been annealed.

3. A method of making a prosthetic device having an external surface with an external skin layer, the method comprising the steps of:
   forming an external covering according to claim 1, the external covering including the external skin layer and the internal bulk layer; and
   fastening the internal bulk layer of the external covering to an internal endoskeleton.

4. The method of claim 3, further comprising the step of applying a powder to the external skin layer, the powder providing superhydrophobicity to the external skin layer.

5. The method of claim 3, further comprising the step of annealing the carbon nanotubes prior to the nanotubes being embedded into the polymer composite of the film.

6. The method of claim 1, wherein the method further comprises the step of embedding a biosensor in the internal bulk layer proximate to the shaped film.

7. The method of claim 1, wherein the step of inserting a film comprised of a polymer composite with carbon nanotubes embedded therein uses a polymer composite in which the carbon nanotubes are vertically aligned between the first side and the second side.

8. The method of claim 1, wherein the step of inserting a film comprised of a polymer composite with carbon nanotubes uses a polymer composite that comprises at least one selected from the group of polyimides, fluoropolymers, polyamides, polyesters, silicones, polyurethanes, epoxies, and polyacrylates.

9. The method of claim 1, wherein the step of applying one selected from the group of heat, vacuum, pressure, or a combination thereof to the cavity or the film applies heat to melt or deform the film to induce the formation of the cone-shaped projections.

10. The method of claim 1, wherein the step of inducing the formation of cone-shaped projections by applying heat, vacuum, pressure, or a combination thereof to the cavity or the film induces the formation of one selected from the group of nanometer sized nano-cones and micrometer sized micro-cones.

11. The method of claim 1, wherein the step of inserting the film comprised of a polymer composite with carbon nanotubes embedded therein uses a film having between about 1% and about 40% carbon nanotubes by volume.

12. The method of claim 1, wherein the step of inserting a film comprised of a polymer composite with carbon nanotubes embedded therein uses carbon nanotubes whose size, shape, and length are selected to provide a predetermined color shade that matches the color associated with a person's skin.

13. The method of claim 3, wherein the step of back-molding the internal bulk layer uses a material that adheres to the film and provides for physical protection of the underlying endoskeleton.

14. The method of claim 1, wherein the increase in Young's modulus is between about 15% and 40%; the increase in hardness is between about 17% and about 25%, the decrease in polymer creep is between about 8% and about 20%, and the increase in scratch resistance is between about 58% and about 90% when the polymer composite contains about 10 wt. % of the carbon nanotubes.

15. The method of claim 1, wherein the increase in Young's modulus is up to about 320%, the increase in hardness is up to about 134%, and the reduction in polymer creep is up to as much as 116% when the polymer composite contains about 40 wt. % of the carbon nanotubes.

16. The method of claim 2, wherein the increase in Young's modulus is between about 22% and 80%; the increase in hardness is between about 22% and about 34%, and the decrease in polymer creep is between about 13% and about 29% for the external skin layer in which the polymer composite contains about 10 wt. % of the annealed carbon nanotubes nanotubes as compared to the external covering in which the polymer composite film is absent the embedded carbon nanotubes.

17. The method of claim 1, wherein the external skin layer further comprises multiple layers of the polymer composite with the embedded carbon nanotubes oriented in different directions along with or without layers of the polymer composite that are absent of any carbon nanotubes.

* * * * *